(12) United States Patent
Weiner et al.

(10) Patent No.: US 7,641,677 B2
(45) Date of Patent: Jan. 5, 2010

(54) COMPRESSION BONE FRAGMENT WIRE

(75) Inventors: Lon S. Weiner, Rumson, NJ (US);
Thomas Coull, Rancho Palos Verdes, CA (US)

(73) Assignee: OrthoPediatrics Corp., Warsaw, IN (US)

( * ) Notice: Subject to any disclaimer, the term of this patent is extended or adjusted under 35 U.S.C. 154(b) by 1330 days.

(21) Appl. No.: 10/300,078

(22) Filed: Nov. 20, 2002

(65) Prior Publication Data
US 2004/0097941 A1    May 20, 2004

(51) Int. Cl.
*A61B 17/86* (2006.01)
(52) U.S. Cl. .......................... 606/315; 606/60; 606/86; 606/301; 411/389; 411/413
(58) Field of Classification Search .............. 606/60, 606/65, 72, 73, 59, 64, 86, 105, 263; 411/411–416, 411/388–389
See application file for complete search history.

(56) References Cited
U.S. PATENT DOCUMENTS
2,393,694 A    1/1946    Kirschner
(Continued)

FOREIGN PATENT DOCUMENTS
WO    WO 92/04875    4/1992
(Continued)

OTHER PUBLICATIONS
Fabory Catalog p. 4-39, "Dowel Screws".
(Continued)

*Primary Examiner*—Eduardo C Robert
*Assistant Examiner*—Mary Hoffman
(74) *Attorney, Agent, or Firm*—Matthew R. Schantz; Bingham McHale LLP (57) ABSTRACT

A bone fragment wire connects a bone fragment to an anchor bone for a healing duration. The bone fragment wire has a distal bone penetration section which is advanced into the bone and a proximal bone exterior section. The proximal bone exterior section is longer than the bone penetration section, and thus extends substantially out of the bone during healing of the bone. The bone penetration section includes a distal bone anchor section which threadingly engages the anchor bone, and a proximal fragment section of small diameter. The fragment section fits within the overbore created by advancing the bone anchor section through the bone fragment, and thus extends through but does not positively engage the bone fragment. A compression engagement on a distal end of the bone exterior section provides a compression shoulder. In one embodiment the compression engagement is provided by a threaded compression nut, while in another embodiment the compression engagement is permanently affixed to the bone wire. The shoulder makes substantial contact with an exterior surface of the bone fragment, biasing the bone fragment toward the anchor bone with a controlled compression force. The compression engagement is further adapted, such as through thread form and/or with a sloped proximal side, to enable the bone wire to be more easily removed from the healed fracture without damaging surrounding tissue.

25 Claims, 3 Drawing Sheets

U.S. PATENT DOCUMENTS

| | | | | |
|---|---|---|---|---|
| 3,256,661 A * | 6/1966 | Fischer | ................ | 52/373 |
| 4,175,555 A | 11/1979 | Herbert | ................ | 128/92 |
| 4,450,835 A | 5/1984 | Asnis et al. | ................ | 128/92 EB |
| 4,456,005 A | 6/1984 | Lichty | | |
| 4,463,753 A | 8/1984 | Gustilo | ................ | 128/92 |
| 4,628,921 A | 12/1986 | Rousso | ................ | 128/92 Z |
| 4,723,541 A | 2/1988 | Reese | ................ | 128/92 |
| 4,854,311 A | 8/1989 | Steffee | ................ | 128/92 YM |
| 4,858,601 A | 8/1989 | Glisson | ................ | 128/92 R |
| RE33,348 E | 9/1990 | Lower | ................ | 606/65 |
| 4,964,403 A | 10/1990 | Karas et al. | | |
| 5,019,079 A | 5/1991 | Ross | ................ | 606/72 |
| 5,129,901 A * | 7/1992 | Decoste | ................ | 606/73 |
| 5,139,500 A | 8/1992 | Schwartz | | |
| 5,180,382 A | 1/1993 | Frigg et al. | ................ | 606/65 |
| 5,226,766 A | 7/1993 | Lasner | ................ | 411/308 |
| 5,259,398 A | 11/1993 | Vrespa | ................ | 128/898 |
| 5,403,136 A | 4/1995 | Mathys | ................ | 411/310 |
| 5,409,486 A | 4/1995 | Reese | ................ | 606/73 |
| 5,417,533 A | 5/1995 | Lasner | ................ | 411/126 |
| 5,492,442 A | 2/1996 | Lasner | ................ | 411/426 |
| 5,562,661 A | 10/1996 | Yoshimi et al. | | |
| 5,562,672 A | 10/1996 | Huebner et al. | ................ | 606/73 |
| 5,580,352 A | 12/1996 | Sekel | ................ | 623/23 |
| 5,609,595 A | 3/1997 | Pennig | ................ | 606/73 |
| 5,613,968 A * | 3/1997 | Lin | ................ | 606/320 |
| 5,669,592 A * | 9/1997 | Kearful | ................ | 248/217.4 |
| 5,676,703 A | 10/1997 | Gelbard | ................ | 606/305 |
| 5,709,687 A * | 1/1998 | Pennig | ................ | 606/73 |
| 5,871,486 A | 2/1999 | Huebner et al. | ................ | 606/73 |
| 5,964,768 A | 10/1999 | Huebner | ................ | 606/73 |
| 5,968,046 A | 10/1999 | Castleman | | |
| 5,989,255 A | 11/1999 | Pepper et al. | | |
| 6,001,101 A | 12/1999 | Augagneur et al. | ................ | 606/73 |
| 6,030,162 A | 2/2000 | Huebner | ................ | 411/413 |
| 6,099,529 A | 8/2000 | Gertzman et al. | | |
| 6,129,730 A | 10/2000 | Bono et al. | ................ | 606/73 |
| 6,159,210 A | 12/2000 | Voor | ................ | 606/56 |
| 6,162,225 A | 12/2000 | Gertzman et al. | | |
| 6,238,417 B1 | 5/2001 | Cole | | |
| 6,261,292 B1 | 7/2001 | Diebold et al. | ................ | 606/73 |
| 6,306,140 B1 | 10/2001 | Siddiqui | ................ | 606/73 |
| 6,338,732 B1 | 1/2002 | Yang | | |
| 6,348,053 B1 | 2/2002 | Cachia | ................ | 606/72 |
| 6,511,481 B2 | 1/2003 | Von Hoffmann et al. | ................ | 606/67 |
| 6,562,046 B2 * | 5/2003 | Sasso | ................ | 606/96 |
| 6,632,224 B2 | 10/2003 | Cachia et al. | ................ | 606/72 |
| 6,648,890 B2 | 11/2003 | Culbert et al. | ................ | 606/63 |
| 6,685,706 B2 | 2/2004 | Padget et al. | ................ | 606/72 |
| 2002/0143335 A1 * | 10/2002 | von Hoffmann et al. | ................ | 606/67 |

FOREIGN PATENT DOCUMENTS

WO      WO 00/40164      7/2000

OTHER PUBLICATIONS

Depuy/Johnson & Johnson Gateway, LLC, "Rockwood Clavicle Pin", www.jnjgateway.com, 2 pages.

Depuy/Johnson & Johnson Gateway, LLC,, "Bone Screws and Pins, Essential Product Information", www.jnjgateway.com, 2 pages.

Depuy/Johnson & Johnson Gateway, LLC, "Rockwood Clavicle Pin, Case X-Rays", www.jnjgateway.com, 2 pages.

Depuy/Johnson & Johnson Gateway, LLC, "Rockwood Clavicle Pin, Design Rationale", www.jnjgateway.com, 2 pages.

Depuy/Johnson & Johnson Gateway, LLC, "Rockwood Clavicle Pin, Surgical Technique", www.jnjgateway.com, 11 pages.

Depuy/Johnson & Johnson Gateway, LLC, "Rockwood Clavicle Pin, Post Operative Care", www.jnjgateway.com, 2 pages.

Beaumont Hospitals, "Athletes pinning their hopes on new procedure", www.beaumonthospitals.com, 2 pages.

Wheeless, "IM Pin Fixation of Clavicle Frx", www.wheelessonline.com, 4 pages.

Carl J. Basmania M.D., IM Pin Fixation of Clavicle Frx.; Wheeless Textbook of Orthopaedics; Aug. 26, 2004; pp. 1-4, http://www.wheelessonline.com/orthoo/5100.htm.

* cited by examiner

COMPRESSION BONE FRAGMENT WIRE

CROSS-REFERENCE TO RELATED APPLICATION(S)

None.

BACKGROUND OF THE INVENTION

The present application is directed to bone pins and wires, and, more specifically, to bone pins and wires used to attach a bone fragment to an anchor bone for a healing duration.

Bone pins and wires are characterized by having a relatively small diameter, such as a diameter less than 0.1 inch (2.5 mm). Bone pins which are elongated wires are commonly referred to as "Kirschner wires" or "K-wires". An example of this is disclosed in U.S. Pat. No. 2,393,694 to Kirschner. The term "bone pin" is more commonly used for shorter structures, such as a length of 2 inches or less, while the term "K-wire" more commonly applies to longer structures, such as a length up to 12 inches, but there is no bright line definition clearly distinguishing between a "bone pin" and a "K-wire" based on length. The present application uses the term "bone wire" to refer to such a small diameter structure and including either a bone pin or a K-wire, regardless of length, but excluding, for instance, a larger diameter bone screw.

Such bone wires have long been used in the orthopaedic arts for several different purposes. Bone wires are often used during surgery as a temporary guide in targeting and directing another more permanent device, such as a cannulated bone screw running over the bone wire, into a bone fragment or anchor bone. Bone wires have been implanted to anchor other devices, such as a bone plate, fixator or external splint device, to a fractured bone. Bone wires have also been used to secure many types of bone fragments to anchor bones, where the term bone "fragment" refers to any part of bone separated by a fracture, regardless of whether that fracture is partial or completely through the bone.

Bone wires commonly have a pointed tip, which may be further fabricated with a drill type structure such that rotation of the bone wire about its longitudinal axis helps to remove bone material from the hole into which the bone wire is advanced. The bone wires may or may not have fine threads to further assist in axially advancing the bone wire into its hole during rotation. While bone wires have been used for fragment fixation, design improvements are needed to have a small diameter bone wire structure which more easily places an appropriate compression force on the interface between the bone fragment and its anchor bone.

BRIEF SUMMARY OF THE INVENTION

The present invention is a bone fragment wire for connecting a bone fragment to an anchor bone for a healing duration. The bone fragment wire has a bone penetration section which is advanced into the bone. The bone fragment wire has a bone exterior section which extends substantially out of the bone during healing of the bone. The bone penetration section includes a distal bone anchor section which threadingly engages the anchor bone, and a fragment section which extends through but does not positively engage the bone fragment. The fragment section thus fits within the overbore created by advancing the bone anchor section through the bone fragment. A compression engagement on a distal end of the bone exterior section provides a compression shoulder. The shoulder makes substantial contact with an exterior surface of the bone fragment, biasing the bone fragment toward the anchor bone with a controlled compression force.

While the above-identified drawing figures set forth preferred embodiments, other embodiments of the present invention are also contemplated, some of which are noted in the discussion. In all cases, this disclosure presents the illustrated embodiments of the present invention by way of representation and not limitation. Numerous other minor modifications and embodiments can be devised by those skilled in the art which fall within the scope and spirit of the principles of this invention.

DETAILED DESCRIPTION

A preferred fragment bone wire 10 of the present invention includes an anchor section 12 located distally of an intermediate fragment section 14. A compression section 16 is provided proximally of the intermediate fragment section 14, and a rotation section 18 is provided proximally of the compression section 16. In the surgical method of using the bone wire 10, the anchor section 12 and the fragment section 14 penetrate the bone 20, while the compression section 16 and the rotation section 18 remain outside on the exterior of the bone 20. The bone penetrating section 22, i.e., the anchor section 12 and the fragment section 14, are shorter in combined length than the combined length of the bone exterior section 24, i.e., the compression section 16 and the rotation section 18.

The distal anchor section 12 has a shaft portion 26 terminating in a drill tip 28. The hole which is made in the fragment 30 and the anchor bone 32 for the bone wire 10 is generally not pre-drilled, but rather is drilled by the drill tip 28 during advancement of the bone wire 10 through the fragment 30 and into the anchor bone 32. The drill tip 28 may be constructed in accordance with drill tip techniques used on current bone wires, such as a three-sided sharp trocar. As known in the art, this drill tip 28 assists the bone wire 10 in drilling a hole through bone 20, breaking up bone 20 and removing bone powder and minute bone pieces from the hole during drilling.

The shaft portion 26 includes anchor threads 34, which serve both to advance the bone wire 10 into the anchor bone 32 during rotation, and to anchor the bone wire 10 into the anchor bone 32 after implantation is completed. The shaft portion 26 has a relatively short length suitable for anchoring in a desired anchor bone 32. The shaft portion 26 of the distal anchor section 12 may have a length of 5 mm for about a five millimeter anchor. During use, the bone wire 10 is advanced through a fragment 30 and into an anchor bone 32 until the distal anchor section 12 is substantially entirely within the anchor bone 32. The anchor threads 34 are constructed with an appropriate width and pitch to suitably perform the advancing and anchoring functions in a bone wire 10 with its small diameter. For instance, the anchor threads 34 in a preferred "thin" embodiment have a minor diameter of 1.65 mm and a major diameter of 2 mm. In a preferred "thick" embodiment, the anchor threads 34 have a minor diameter of 2 mm and a major diameter of 2.35 mm. The anchor threads 34 in a preferred embodiment have a pitch of 0.5 mm per rotation.

Since the fragment 30 and the anchor bone 32 are not typically predrilled, the hole for the bone wire 10 in the fragment 30 and anchor bone 32 is not typically pre-tapped. Thus, the anchor threads 34 are preferably self-tapping on the distal side of the anchor section 12, as commonly known in the screw thread art. Having the anchor threads 34 be self-tapping for insertion decreases the number of surgical steps and surgery time as compared to tapping with a separate tap, while providing a firmer attachment with less bone damage and requiring less drill force as compared to not tapping at all.

The bone wire 10 of the present invention is intended to be surgically implanted and left within the patient for a healing duration while the fragment 30 attaches and grows together to the anchor bone 32. During this bone growth healing duration, bone tissue may grow back within the threads cut into the fragment 30 by the anchor threads 34. To assist in removing the anchor section 12 through the fragment 30 after the healing duration, the preferred threads 34 are self-tapping on the proximal side as well. Having the threads 34 be self-tapping on the proximal side reduces the torque necessary for removal, decreasing the likelihood of shearing breakage of the bone wire 10 during removal and decreasing the likelihood of damage to the surrounding bone and surrounding tissue during removal.

Figure 2:
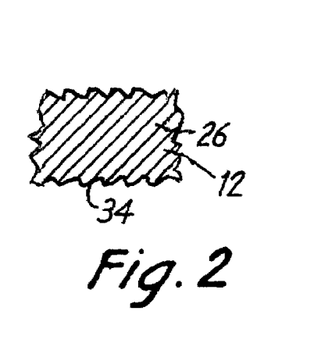
FIG. 2 is a cross sectional view of the threads/nuts taken at area 2 of FIG. 1.

As shown in FIG. 2, the preferred anchor threads 34 have a thread form which is angled against pull-out. The angle of the thread form can significantly increase the pull-out force which can be supported by the bone wire 10, which can be very important especially if the anchor bone 32 is weak, damaged or overly pourous.

The fragment section 14 has a diameter which is smaller than at least the major diameter of the anchor section 12, and preferably smaller than the minor diameter of the anchor section 12 as well. Being smaller in diameter, the fragment section 14 does not interfere with the hole in the fragment 30 created by the anchor section 12 when the anchor section 12 was advanced through the fragment 30. For instance, the fragment section 14 may have a smooth cylindrical profile, contrasted against the threaded anchor section 12. In the preferred "thin" embodiments, the fragment section 14 has a smooth cylindrical profile with a diameter of 1.5 mm. The fragment section 14 thus follows behind the minor diameter on the threaded anchor section 12 of 1.65 mm and does not substantially engage the bone of the fragment 30. In the preferred "thick" embodiment, the fragment section 14 has a smooth cylindrical profile with a diameter of 1.85 mm. The fragment section 14 thus follows behind the minor diameter on the threaded anchor section 12 of 2 mm and does not substantially engage the bone of the fragment 30. With the small diameter of the fragment section 14, the bone wire 10 of the present invention can be thought of as having a reverse taper, with the proximal fragment section 14 of the wire 10 being narrower in diameter than the distal anchor section 12.

The length of the fragment section 14 should approximately correspond with the length of the fragment 30 in the injured bone 20. Obviously, the length of the fragment 30 depends upon the injury, and is not the same for all fractured bones. Particularly for "thin" embodiments, the bone wire 10 may be provided as part of a kit which allows the surgeon to select the length of the fragment section 14 as desired for a particular fragment 30. For instance, the kit may include bone wires 10 with fragment section lengths that vary in 2 mm increments, i.e., lengths for the fragment section 14 of 2, 4, 6, 8, 10, 12, 14 and 16 mm.

The compression section 16 provides a compression engagement 36 which defines the proximal extent of the fragment section 14. The purpose of the compression engagement 36 is to place a compression force on an exterior surface of the bone fragment 30, and thus externally bias the bone fragment 30 toward the anchor bone 32. The compression engagement 36 includes a shoulder surface 38 extending at a substantial angle to the wire axis for substantial contact with an exterior surface of the bone fragment 30. The bone wire 10 thus allows for compression via the compression engagement 36 after insertion through the skin and placement of the compression engagement 36 against the bone fragment 30.

Figure 1:
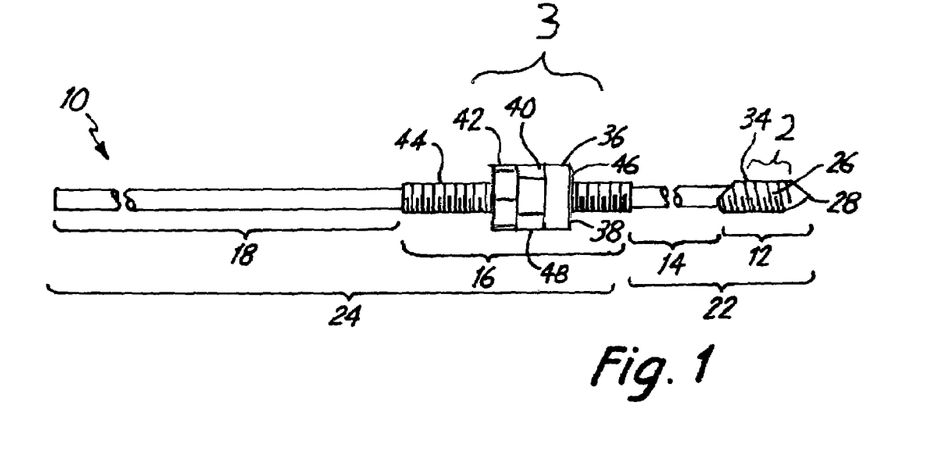
FIG. 1 is a side view of a first embodiment of the invention.
Figure 3:
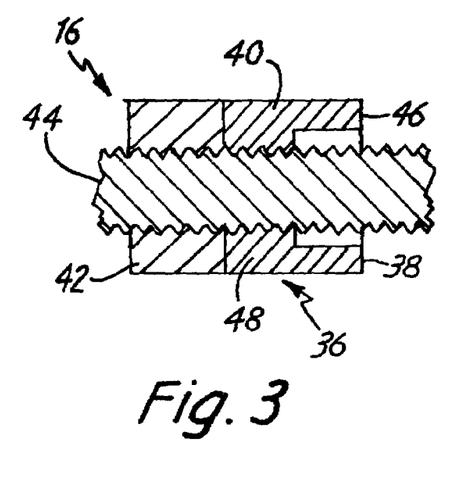
FIG. 3 is a cross sectional view of the threads taken at area 3 of FIG. 1.

In the embodiment of FIGS. 1-3, the compression engagement 36 is provided by one or more nuts 40, 42 placed on a proximal threaded shaft section 44. A preferred length for the proximal threaded shaft section 44 is 15 mm. The preferred compression nut 40 has a compression shoulder section 46 and a drive section 48. The compression shoulder section 46 is on the distal side of the nut 40 and has a cylindrical outer profile, such as an outer diameter of 4 mm. The compression shoulder section 46 has an inside bore, which is large enough to fit over both the proximal threaded shaft section 44 and the fragment section 14. For instance, the inside bore may be a smooth cylindrical hole with a 1.85 mm diameter. The length of the compression shoulder section 46 may be designed as desired to correspond with the amount of adjustment and flexibility desired. If kits of bone wires 10 are provided with a 2 mm variance in length of fragment sections 14, then the length of the compression shoulder section 46 may match this variance, i.e., extend axially for at least 2 mm.

The drive section 48 is on the proximal side of the nut 40 to enable the surgeon to rotationally advance the compression nut 40 with a standard tool. For instance, the drive section 48 of the compression nut 40 may have a traditional hexagonal profile with a distance between opposing flats of about 3.45 mm. The drive section 48 is internally threaded to mate with the external threads of the proximal threaded shaft section 44, such as a threaded length of 4 mm. If desired, a lock nut 42 may be further used to secure the compression nut 40 at a desired axial position, such as a lock nut 42 of 2 mm.

Figure 4:
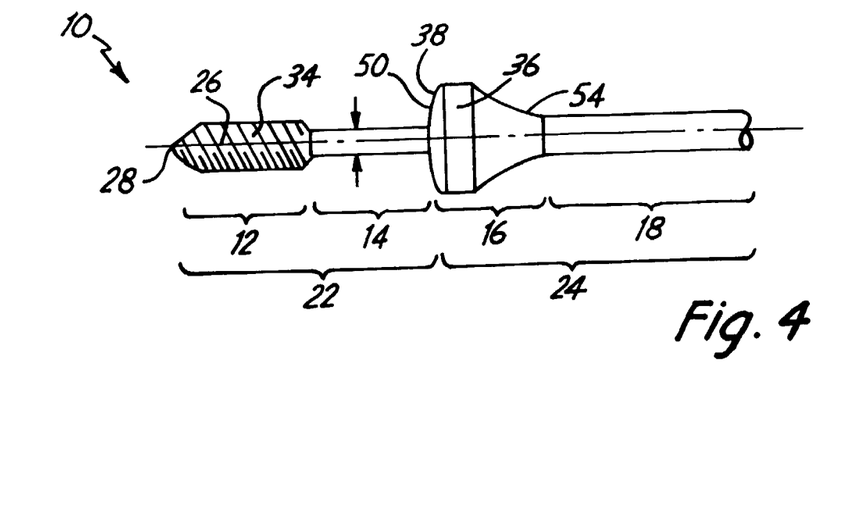
FIG. 4 is a side view of the second embodiment of the invention.
Figure 5:
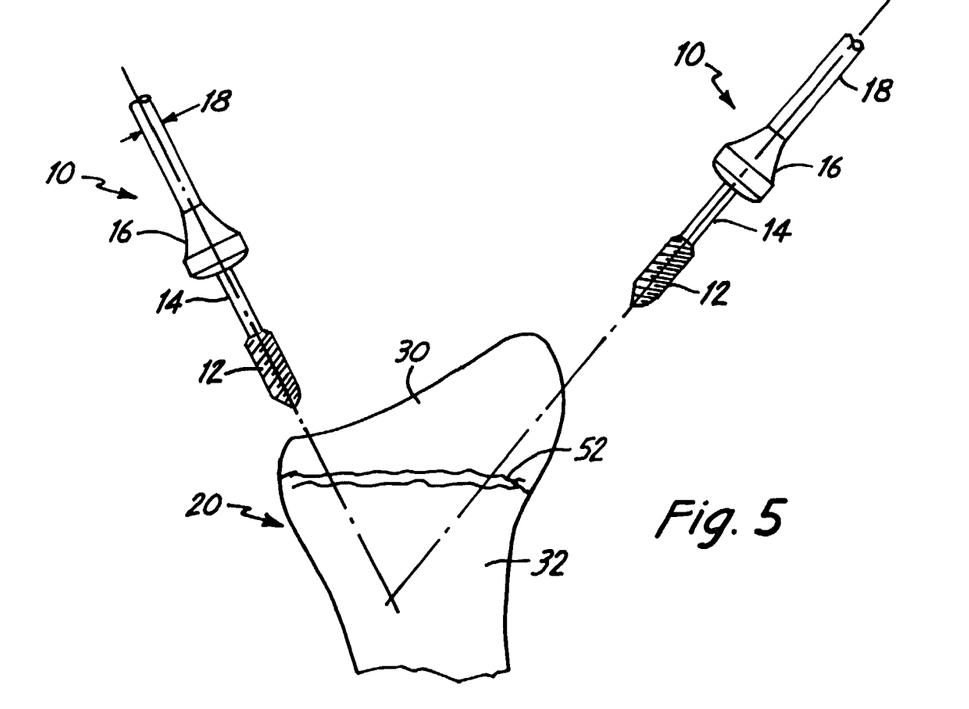
FIG. 5 is a side view of the second embodiment of the invention during implantation with a fractured bone.
Figure 6:
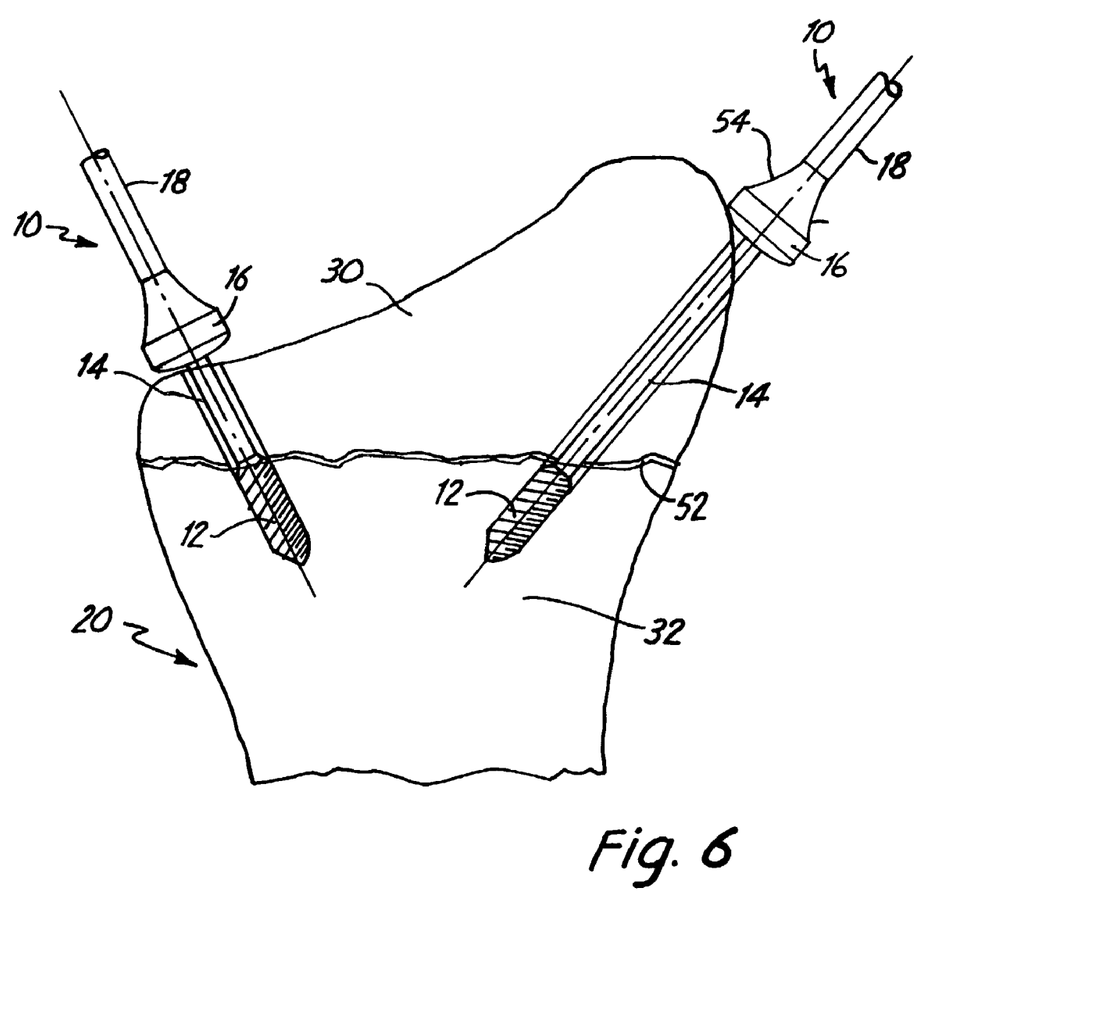
FIG. 6 is a side view of the second embodiment of the invention after implantation.

In the embodiment of FIGS. 4-6, the compression engagement 36 is a tear-drop shoulder 50. In contrast with the compression nut 40, the tear-drop shoulder 50 is integrally formed or permanently affixed to the rest of the bone wire 10.

With either the compression nut 40 or the tear-drop shoulder 50, a distal shoulder surface 38 is provided for contact with the exterior surface of the bone fragment 30. The distal shoulder surface 38 preferably has a curvature of large radius, for enhancing the likelihood of a smooth engagement with the exterior surface of the fragment 30. If desired, the bone wire 10 may be included as part of a kit with several different compression engagements 36 each having a different radius of curvature on the distal shoulder surface 38, enabling the surgeon to pick the compression engagement 36 having a distal shoulder surface 38 which best matches the surface of the bone fragment 30. The intent is to support the compression force with a broad surface to surface contact between the compression engagement 36 and the bone fragment 30 rather than at a point contact which could dig into and damage the bone fragment 30.

Because the fragment section 14 has too small a diameter to positively engage the fragment 30, the compression shoulder 38 provides substantially all of the force pressing the bone fragment 30 into the anchor bone 32 during the healing duration. The present invention permits control of this compression force in either of two ways. First, the compression force can be selected by the surgeon by determining how far to rotationally advance the bone wire 10 into the anchor bone 32, while the compression shoulder 38 remains at a constant longitudinal position relative to the bone wire 10. In the embodiment of FIGS. 1-3 and depending upon the relative frictional forces involved, supplying a compression force in this manner may require the surgeon to positively rotate the compression nut 40 during rotation of the bone wire 10. In the embodiment of FIGS. 4-6, the tear-drop shoulder 50 is integrally formed or permanently secured to the bone wire 10, so the surgeon need not take any further steps other than rotating the bone wire 10, and the compression shoulder 38 will always advance with the rotating bone wire 10.

Second, in the embodiment of FIGS. 1-3, the compression force can be selected by the surgeon after the bone wire 10 is fully advanced into the anchor bone 32, by rotationally advancing the compression nut 40 relative to a stationary bone wire 10. This allows the surgeon to customize the bone wire 10 as to the length between the tip 28 of the bone wire 10 and the compression shoulder 38. Depending upon the relative frictional forces involved, supplying a compression force in this manner may require the surgeon to positively hold the bone wire 10 in a non-rotating position during rotation of the compression nut 40.

With either embodiment, the surgeon can monitor the amount of compression force being applied in any of several different ways. First, the surgeon may be able to visually (either directly or with the aid of scoping equipment) see advancement of the fragment 30 toward the anchor bone 32. Note, for instance, that FIG. 5 shows the fragment 30 separated from the anchor bone 32 by a slight gap 52, and FIG. 6 shows the fragment 30 having been moved against the anchor bone 32 to completely close the gap 52. Second, the surgeon may have the sensitivity to feel the change in torque associated with advancing the compression shoulder 38 against the fragment 30, either by hand or with the aid of a monitoring tool such as a torque wrench. Such "feel" of the advancing torque requirements is relatively easy with the embodiment of FIGS. 1-3 if the bone wire 10 is stationary; otherwise, the surgeon must be careful to distinguish between any change in torque required to rotationally advance the bone wire 10 as distinguished from any change in torque required to rotationally advance the compression shoulder 38. Third, the amount of torque applied in advancing the compression shoulder 38 can be controlled below a maximum threshold value. Either a drill having a controlled or set maximum torque can be used, or the rotational engagement structure (for instance, the flats of the compression nut 40) can be designed to shear off at a desired torque. In practice, all three methods may be used simultaneously.

The embodiment of FIGS. 1-3 can provide a further benefit, provided that a proximal threaded shaft section 44 which supports the nut 40 is made long enough and of small enough diameter. Namely, the proximal threaded shaft section 44 can be substantially longer than the desired amount of compression movement. Provided the proximal threaded shaft section 44 will fit within the overbore of the fragment 30 created by the anchor section 12, the bone wire 10 may be advanced until a substantial portion of the proximal threaded shaft section 44 resides within the fragment 30. The selectable length of the fragment section 14 is then not as critical. For instance, a preferred length for the proximal threaded shaft section 44 in the embodiment of FIGS. 1-3 is 15 mm, while the preferred compression nut 40 together with the lock nut 42 have an axial length of only 8 mm. Provided the diameter of the proximal threaded shaft section 44 permits it to fit within the overbore drilled by the anchor section 12, then up to 7 mm of the proximal threaded shaft section 44 can be placed within the overbore in the fragment 30. The compression nut 40 can be advanced until at least the compression shoulder section 46 extends over the fragment section 14, i.e., axially for 2 mm beyond the end of the proximal threaded shaft section 44, for a total range of compression motion for the compression shoulder 38 of 9 mm. With this large range of compression motion for the compression shoulder 38, the kit need only include fragment sections 14 with a length variance of the total range of compression motion, e.g., a kit with fragment sections 14 of 2, 11 and 20 mm would allow use on a fragment 30 of anywhere from 0 to 27 mm in thickness. If the length of the proximal threaded shaft section 44 was lengthened to 33 mm, then a single bone wire 10 with a fragment section 14 of 2 mm could be used on fragments 30 of 0 to 27 mm in thickness.

However, the tradeoff for this flexibility in length lies in the strength of the bone wire 10. In particular, if the fragment section 14 has a diameter of 1.5 mm, then the major diameter of the proximal threaded shaft section 44 should be 1.5 mm or less to fit within the overbore in the fragment 30 to the same extent as the fragment section 14 fits within the overbore. If the thread depth is retained at at least 0.15 mm, and major diameter of 1.5 mm results in a minor diameter of no greater than 1.2 mm. However, the minor diameter must be strong enough to support the required torque to drive the anchor section 12 through the fragment 30 and through the anchor bone 32. With current materials, a minor diameter of 1.2 mm over a 33 mm length results in a brittle, weak product, which is likely to break off during driving through the bone 20 or during use.

Instead, the preferred embodiments of the bone wire 10 retain a minimum diameter of at least 1.5 mm throughout. The major diameter of the proximal threaded shaft section 44 is accordingly selected at 1.83 mm. This major diameter interferes with the minor diameter of 1.65 mm drilled by the "thin" anchor section 12, and hence the bone wire 10 should be used without advancing any part of the proximal threaded shaft section 44 into the fragment bore. Given that no part of the proximal threaded shaft section 44 extends into the fragment bore, the compression nut 40 only has 2 mm of axial advancement flexibility, and the bone wires 10 are thus provided in kits of 2 mm variance in length of fragment sections 14. The major diameter for the proximal threaded shaft section 44 of 1.83 mm does not interfere with the minor diameter of 1.85 mm drilled by the "thick" anchor section 12. As such, the proximal threaded shaft section 44 can extend into the fragment bore drilled by the "thick" anchor section 12, and the compression nut 40 in the preferred "thick" embodiment has a full 9 mm of axial advancement flexibility.

The rotation section 18 of the bone wire 10 extends substantially beyond the end of the compression section 16. In most uses, the rotation section 18 will extend outside the patient's skin during the entire healing duration, which can greatly facilitate healing. The rotation section 18 allows the bone wire 10 to be rotated without interference with tissue adjacent the bone 20, so the surrounding tissue is less damaged during surgery than occurred with prior art methods. The rotation section 18 allows the bone wire 10 to be used in fixating the fracture with a fixator support structure as described in U.S. Pat. Nos. 6,058,748, 6,283,946, and U.S. patent application Ser. No. 10/160,470, incorporated by reference, which can allow the proper amount of stress to be placed on the bone 20 during healing, substantially benefitting the healing process. The fixator support structure attaches to the rotation section 18 of the bone wire 10. The placement of the compression shoulder 38 against the fragment 30 also increases the fixation by reducing wire toggle, such as may occur during wrist motion. In the preferred embodiment, the rotation section 18 is cylindrical with a diameter of 1.5 mm, and extends for 100 to 150 mm.

The present invention includes several features which are specifically directed to removal of the bone wire 10 after the healing duration. In contrast to most bone pins and bone screws, the bone wire 10 of the present invention leaves a significant length exposed through the skin to grasp for removal without damaging tissue. In the embodiment of FIGS. 1-3, the threads of the proximal threaded shaft section 44 have a different pitch and a different shape than the anchor threads 34. For instance, the proximal threaded shaft section 44 may have a pitch of 0.4 mm per revolution, as compared to the preferred anchor thread pitch of 0.5 mm. Counterclockwise rotation of the bone wire 10 will cause the bone wire 10 to retract its anchor thread pitch, i.e., 0.5 mm per revolution. Because the proximal threaded shaft section 44 has a shallower pitch than the anchor threads 34, the nut(s) 40, 42 must retract with counterclockwise rotation of the bone wire 10. That is, the nut(s) 40, 42 could rotate with the rotating bone wire 10, in which case the nut(s) 40, 42 would retract at the anchor thread pitch, i.e., 0.5 mm per revolution. Alternatively, even if the surrounding tissue has grown around the nut(s) 40, 42 and prevents rotation of the nut(s) 40, 42, the nut(s) 40, 42 will still back out at the difference between pitches, i.e., 0.1 mm per revolution of the bone wire 10. Further, if the compression nut 40 rotates all of the way to the distal end of the proximal threaded shaft section 44, the compression nut screw thread has a smaller inside diameter than the outside diameter of the fragment section 14, preventing the compression nut 40 from further advancing onto the fragment section 14.

As shown in FIG. 3, the proximal threaded shaft section 44 may have a thread form which is balanced in both proximal and distal directions, in contrast to the preferred anchor threads 34 which have a thread form which is angled against pull-out. Alternatively, the thread form for the proximal threaded shaft section 44 may be angled oppositely to the thread form of the preferred anchor threads 34, to better support the compression force placed on the compression nut 40.

In the embodiment of FIGS. 4-6, the proximal surface 54 of the tear-drop shoulder 50 assists in removal of the bone wire 10 through tissue which may grow around the bone exterior section 24 of the bone wire 10 during the healing duration. In particular, the proximal surface 54 of the tear-drop shape is sloped for removal, with the slope angle being shallow near the axis of the bone wire 10, becoming steeper at intermediate diameters, and then again becoming shallow near the maximum diameter of the tear-drop shoulder 50. This shape helps to separate the overlying tissue with minimal damage to such surrounding tissue when the bone wire 10 is removed. In the embodiment of FIGS. 1-3, the proximal surface of the compression nut 40 and/or the lock nut 42 could alternatively be modified to provide a similar slope for assisting in separating overlying tissue during removal.

Because of the various features of the bone wire 10 of the present invention which facilitate removal, removal of the bone wire 10 can be accomplished without requiring a separate incision to be made after the healing duration. Avoiding this additional incision greatly helps in healing the tissue over the fractured bone 20, both in terms of the length of time required for full healing and in terms of avoiding the build-up of scar tissue.

The bone wire 10 may be formed out of any surgically acceptable strong material, such as surgical acceptable stainless steel (such as 316 LVM, per ASTM F1350, electropolished and passivated) or a titanium alloy (such as TI-6AL-4V, per ASTM F136).

The method of use of the bone wire 10 of the present invention should be readily apparent in the preceding discussion, and will be further outlined here. Insertion of the bone wire 10 is performed through a small incision with blunt dissection carried to the bone 20. For insertion, the bone wire 10 is drilled through the fragment 30, and the thicker diameter anchor threads 34 overbore a hole through the fragment 30. The thicker diameter anchor threads 34 then reach the anchor bone 32 and pull the bone wire 10 axially forward. Drilling through a sheath (not shown) helps protect surrounding tissue so that the threads 34 do not damage nearby soft tissue. Once the narrower fragment section 14 of the bone wire 10 extends through the fragment 30, the bone wire 10 is no longer in threaded engagement with the fragment 30. This leaves the compression engagement 36 to bias the fragment 30 toward the anchor bone 32. In the embodiment of FIGS. 1-3, the compression nut 40 can be tightened with a wrench until the compression shoulder 38 engages the exterior surface of the fragment 30 with the desired compression force. After the healing duration, the bone wire 10 is simply removed from the bone 20 by counterclockwise rotation of the rotation section 18, causing as little additional tissue damage as possible.

The present invention can be used on most types of fractures which have previously been treated by percutaneous pinning. Avulsion fractures of the hand and foot as well as reconstruction procedures such as IP fusions and hammertoe correction are excellent applications.

Although the present invention has been described with reference to preferred embodiments, workers skilled in the art will recognize that changes may be made in form and detail without departing from the spirit and scope of the invention. In particular, the specific dimensions mentioned but not required by the claims are exemplary only, and do not limit the claimed invention.

The invention claimed is:

1. A bone fragment wire for connecting a bone fragment to an anchor bone for a healing duration and for extending out of the bone during the healing duration, the bone fragment wire comprising:

an elongated wire having a bone penetration section extending distally from a bone exterior section about a wire axis, the bone penetration section having a distal end and a proximal end with a bone penetration section length therebetween, the bone exterior section having a distal end and a proximal end with a bone exterior section length therebetween, the bone penetration section length being shorter than the bone exterior section length, the bone penetration section including a non-engaging fragment section and a bone anchor section located distally to the non-engaging fragment section, the non-engaging fragment section having a shaft with a shaft diameter of no greater than 0.1 inch, the bone anchor section having threads for engagement with the anchor bone, with a major diameter of the threads being greater than the shaft diameter of the non-engaging fragment section; and a compression engagement on the bone exterior section, the compression engagement providing a shoulder which is longitudinally located at the distal end of the bone exterior section, the shoulder extending at a substantial angle to the wire axis for substantial contact with an exterior surface of the bone fragment; and wherein the bone exterior section has external threads that mate with internal threads on the compression engagement, and wherein the inside diameter of the internal threads on the compression engagement is smaller than the shaft diameter of the non-engaging fragment section such that the internal threads on the compression engagement cannot advance onto the non-engaging fragment section.

2. The bone fragment wire of claim 1, wherein the bone exterior section has threads of a shallower pitch than the threads of the bone anchor section, and wherein the compression engagement is provided by a nut rotatably supported on the threads of the bone exterior section.

3. The bone fragment wire of claim 1, wherein the bone exterior section has threads of a different thread profile than the threads of the bone anchor section, and wherein the compression engagement is provided by a nut rotatably supported on the threads of the bone exterior section.

4. The bone fragment wire of claim 1, provided in a kit of a plurality of bone fragment wires each having a different length of non-engaging fragment section.

5. The bone fragment wire of claim 1, wherein the compression engagement has a proximal side with a sloped profile to assist in removing the compression engagement after a healing duration through tissue.

6. The bone fragment wire of claim 5, wherein a slope of the proximal side of the compression engagement increases from a gentle slope adjacent an outer diameter of the bone exterior section of the wire to a steeper slope distal to the gentle slope, thus providing a compression engagement of generally tear-drop cross-sectional shape.

7. The bone fragment wire of claim 1, wherein the compression engagement is permanently affixed to the wire.

8. The bone fragment wire of claim 1, wherein the shaft of the non-engaging fragment section is substantially smooth and cylindrical.

9. The bone fragment wire of claim 1, wherein the threads on the bone anchor section are self-tapping distally for insertion and self tapping proximally for removal.

10. The bone fragment wire of claim 1, wherein the compression engagement has a tear drop cross-sectional shape, wherein the compression engagement is permanently affixed to the wire, wherein the shaft of the non-engaging fragment section is substantially smooth and cylindrical, and wherein the threads on the bone anchor section are self-tapping distally for insertion and self-tapping proximally for removal.

11. The bone fragment wire of claim 1, wherein the shoulder of the compression engagement has a curvature to contact the exterior surface of the bone fragment along the curvature.

12. The bone fragment wire of claim 1, wherein the bone exterior section comprises:
 a rotation section having a substantially smooth outer surface, and
 a compression section extending distally from the rotation section, the compression section having external threads which mate with internal threads on the compression engagement, with the compression section being shorter than the rotation section.

13. The bone fragment wire of claim 1, wherein the non-engaging fragment section extends axially for 0.08 inch (2 mm) or more.

14. The bone fragment wire of claim 1, wherein the bone anchor section comprises a distal cutting tip for insertion into a bone without pre-drilling.

15. The bone fragment wire of claim 1, wherein a minor diameter of the threads on the bone anchor section is no less than the shaft diameter of the non-engaging fragment section, such that the bone anchor section overbores a hole for the non-engaging fragment section and the non-engaging fragment section does not interfere with bone threads left by advancement of the bone anchor section through a bone fragment.

16. A bone fragment wire for connecting a bone fragment to an anchor bone for a healing duration and for extending out of the bone during the healing duration, the bone fragment wire comprising:
 an elongated wire having a bone penetration section extending distally from a bone exterior section about a wire axis, the bone penetration section having a distal end and a proximal end with a bone penetration section length therebetween, the bone exterior section having a distal end and a proximal end with a bone exterior section length therebetween, the bone penetration section including a non-engaging fragment section and a bone anchor section located distally to the non-engaging fragment section, the non-engaging fragment section being substantially smooth and cylindrical and having a shaft with a shaft diameter of no greater than 0.1 inch, the bone anchor section having threads for engagement with the anchor bone, with a major diameter of the threads being greater than the shaft diameter of the non-engaging fragment section; and
 a compression engagement on the bone exterior section, the compression engagement providing a shoulder which is longitudinally located at the distal end of the bone exterior section, the shoulder extending at a substantial angle to the wire axis for substantial contact with an exterior surface of the bone fragment; and
 wherein the bone exterior section has external threads that mate with internal threads on the compression engagement, and wherein the inside diameter of the internal threads on the compression engagement is smaller than the shaft diameter of the non-engaging fragment section such that the internal threads on the compression engagement cannot advance onto the non-engaging fragment section.

17. The bone fragment wire of claim 16, wherein a slope of the proximal side of the compression engagement increases from a gentle slope adjacent an outer diameter of the bone exterior section of the wire to a steeper slope distal to the gentle slope, such that the compression engagement has a generally tear drop cross-sectional shape.

18. The bone fragment wire of claim 16, wherein the compression engagement is permanently affixed to the wire.

19. The bone fragment wire of claim 16, wherein the threads on the bone anchor section are self-tapping distally for insertion and self tapping proximally for removal.

20. The bone fragment wire of claim 16, wherein the bone penetration section is shorter than the bone exterior section.

21. The bone fragment wire of claim 16, wherein the shaft diameter of the non-engaging fragment section is smaller than a minor diameter of the threads on the bone anchor section.

22. The bone fragment wire of claim 16, wherein the non-engaging fragment section extends axially for 0.08 inch (2 mm) or more.

23. A bone fragment wire for connecting a bone fragment to an anchor bone for a healing duration and for extending out of the bone during the healing duration, the bone fragment wire comprising:
 an elongated wire comprising:
  a bone exterior section, the bone exterior section comprising:

a rotation section having a substantially smooth outer surface, and a compression section extending distally from the rotation section, the compression section having external threads; and a bone penetration section extending distally from a bone exterior section about a wire axis, the bone penetration section comprising:

a non-engaging fragment section having a shaft with a shaft diameter, wherein the shaft of the non-engaging fragment section is substantially smooth and cylindrical; and a bone anchor section located distally to the non-engaging fragment section, the bone anchor section having threads for engagement with the anchor bone, with a major diameter of the threads being greater than the shaft diameter of the non-engaging fragment section; and a compression engagement providing a shoulder which is longitudinally located at a distal end of the bone exterior section, the shoulder extending at a substantial angle to the wire axis for substantial contact with an exterior surface of the bone fragment, the compression engagement having internal threads which mate with the external threads on the compression section, and wherein the inside diameter of the internal threads on the compression engagement is smaller than the shaft diameter of the non-engaging fragment section such that the internal threads on the compression engagement cannot advance onto the non-engaging fragment section.

24. The bone fragment wire of claim 23, wherein the non-engaging fragment section extends axially for 0.08 inch (2 mm) or more.

25. A bone fragment wire for connecting a bone fragment to an anchor bone for a healing duration and for extending out of the bone during the healing duration, the bone fragment wire comprising:

an elongated wire comprising:

a bone exterior section, the bone exterior section comprising:

a rotation section having a substantially smooth and cylindrical outer surface, and a compression section extending distally from the rotation section, the compression section having external threads, the compression section being shorter than the rotation section; and a bone penetration section extending distally from a bone exterior section about a wire axis, the bone penetration section comprising:

a non-engaging fragment section having a shaft diameter; and a bone anchor section located distally to the non-engaging fragment section, the bone anchor section having threads for engagement with the anchor bone, with a major diameter of the threads being greater than the shaft diameter of the non-engaging fragment section; and a compression engagement providing a shoulder which is longitudinally located at a distal end of the bone exterior section, the shoulder extending at a substantial angle to the wire axis for substantial contact with an exterior surface of the bone fragment, the compression engagement having internal threads which mate with the external threads on the compression section, and wherein the inside diameter of the internal threads on the compression engagement is smaller than the shaft diameter of the non-engaging fragment section such that the internal threads on the compression engagement cannot advance onto the non-engaging fragment section.

* * * * *

UNITED STATES PATENT AND TRADEMARK OFFICE
CERTIFICATE OF CORRECTION

PATENT NO. : 7,641,677 B2
APPLICATION NO. : 10/300078
DATED : January 5, 2010
INVENTOR(S) : Weiner et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1294 days.

Signed and Sealed this

Sixteenth Day of November, 2010

David J. Kappos
*Director of the United States Patent and Trademark Office*